United States Patent [19]

Hazard

[11] Patent Number: 5,058,580
[45] Date of Patent: Oct. 22, 1991

[54] PERCUTANEOUS TRACHEOSTOMY TUBE

[76] Inventor: Patrick B. Hazard, 910 Madison Ave., Suite 825, Memphis, Tenn. 38103

[21] Appl. No.: 193,301

[22] Filed: May 11, 1988

[51] Int. Cl.$^5$ ............................................. A61M 16/00
[52] U.S. Cl. ........................... 128/207.15; 128/200.26
[58] Field of Search ..................... 128/207.14, 207.15, 128/200.26

[56] References Cited

U.S. PATENT DOCUMENTS

| | | | |
|---|---|---|---|
| 3,538,918 | 11/1970 | Engelsber et al. | 128/351 |
| 3,682,166 | 8/1972 | Jacobs | 128/145 |
| 3,693,624 | 9/1972 | Shiley et al. | 128/207.15 |
| 3,788,326 | 1/1974 | Jacobs | 128/305 |
| 4,246,897 | 1/1981 | Muto | 128/207.15 |
| 4,278,081 | 7/1981 | Jones | 128/207.15 |
| 4,340,046 | 7/1982 | Cox | 128/200.26 |
| 4,459,984 | 7/1984 | Liegner | 128/207.15 |
| 4,483,337 | 11/1984 | Clair | 128/207 |
| 4,573,460 | 3/1986 | Szachowicz et al. | 128/200.26 |
| 4,588,399 | 5/1986 | Nebergall et al. | 128/207.15 |
| 4,677,978 | 7/1987 | Melker | 128/207 |

OTHER PUBLICATIONS

"Bedside Percutaneous Tracheostomy: Experience with 55 Elective Procedures" by Patrick B. Hazard, M.D., et al.
"Elective Percutaneous Dilatational Tracheostomy" by P. Ciaglia, M.D., et al.
"A Percutaneous Tracheostomy Device" by Frederick J. Toy, M.D., et al.
"Transtracheal Catheter Ventilation: Clinical Experience in 36 Patients" by H. Barry Jacobs, M.D., et al.

"Percutaneous Tracheostomy Introducer Set" by Cook Critical Care Corporation.

Primary Examiner—Edgar S. Burr
Assistant Examiner—Aaron J. Lewis
Attorney, Agent, or Firm—P. C. Richardson; L. C. Akers; R. C. Turner

[57] ABSTRACT

The specification discloses a tracheostomy tube which is specifically designed for percutaneous insertion into a patient's trachea through a stoma in the neck between adjacent cartilages. The tracheostomy tube is inserted with an inner obturator as an assembly in conjunction with the Seldinger technique utilizing a guide wire, a guiding catheter, and dilators. The tracheostomy tube includes a soft, flexible tubular cannula which has a distal portion for insertion within the trachea and a proximal end remaining outside the trachea. The assembly includes a tubular obturator adapted to fit over the guiding catheter and adapted to closely fit within the cannula, and has a tapered distal end which extend beyond the distal end of the cannula. The distal end of the cannula is gradually tapered to form a smooth transition between the cannula and the obturator. The distal portion of the cannula has the end thereof beveled to one side so that the most distal tip of the cannula is narrow, angled and tapered and is introduced by the obturator generally midway between the adjacent cartilages. Once the narrow tip of the cannula is clearly inserted between the adjacent cartilages, the remaining angled and tapered distal end of the cannula is readily eased between the cartilages free of interference to facilitate insertion of the assembly. The outer cannula preferably includes a low profile inflatable cuff. The percutaneous tracheostomy tube and preparation and insertion devices are provided in a convenient kit.

22 Claims, 3 Drawing Sheets

PERCUTANEOUS TRACHEOSTOMY TUBE

BACKGROUND OF THE INVENTION

The invention relates to a tracheostomy tube, particularly a tracheostomy tube which is percutaneously inserted between two adjacent cartilages into the trachea of a patient, to assist breathing.

Tracheostomy tubes have been used for some time to provide a bypass supply of air or mixture of gases to a patient having an obstruction in the throat. The distal end of the tracheostomy tube is inserted into the trachea through an incision in the patient's neck below the obstructed area. The proximal end of the tube remains outside the trachea in communication with ambient air to permit passage of such air into the trachea. The proximal end can also be attached to a respiratory device to assist the patient's breathing. The distal end can also include an expandable cuff for forming a seal between the tracheostomy tube and the tracheal wall of the patient to further facilitate breathing on the respiratory device. During operative "standard" tracheostomy, a vertical incision of about 5 cm is made in the mid-line of the neck in the vicinity of the trachea. Cartilages are severed with portions thereof sometimes removed and a relatively large stoma is created for the insertion of the standard tracheostomy tube. The operative procedure usually requires an operating room, general anesthetic and can take 45-60 minutes to perform. The operative procedure further requires transportation to and from an operating room and, due to the surgical stoma, can sometimes lead to infectious complications and cosmetic deformity.

In some installations of tracheostomy type devices, it is possible to insert the device by a technique known as percutaneous insertion. This technique was introduced by Dr. Seldinger in his wire-guided approach to arterial catheterization, and has been widely adapted to other application to include: the placement of trans-tracheal oxygen catheters, tube nephrostomy, drainage of abnormal fluid collections, and epidural catheterization for antiseptic purposes.

One recently described application of the Seldinger technique has been for percutaneous tracheostomy as described in a preliminary report by Dr. P. Ciaglia, et al entitled, "Elective Percutaneous Dilatational Tracheostomy: A New Simple Bedside Procedure" published in Chest Volume 87: 715-719, 1985. The technique is considered to be rapid, technically simple, and remarkably free from technical complications. The brief highlights of the technique include first, a small (about 1 cm) insertion is made below the lower edge of the cricoid cartilage. In conjunction with a local anesthetic, a syringe with an over-the-needle cannula is inserted through the incision into the tracheal lumen. The syringe is then removed and a flexible J-wire guide is inserted and extended downwardly into the trachea. The cannula is then withdrawn and a catheter guide is inserted followed by a series of increasing diameter dilators which are inserted over the guide to expand the stoma. The dilators are removed and a standard tracheostomy tube with one of the dilators used as an inner obturator is then inserted over the guide and into the trachea. The obturator and guide are then removed and the tracheostomy tube is secured to the patient. The various components, as described in the publication by Dr. Ciaglia, to include: the catheter introducer needle, the J-wire guide, dilator, and a series of six increasingly larger curved dilators (12 Fr. to 32 Fr.) have been packaged as "A Percutaneous Tracheostomy Introducer Set" available from Cook Inc., Bloomington, Ind., for percutaneous installation of standard tracheostomy tubes. The components are in a "peel-away" pack which must be opened and then arranged on a surgical tray, along with the preparation components and tracheostomy tube which are not provided.

An Emergency Cricothyrotomy System is described in U.S. Pat. No. 4,677,978 by Richard Melker which incorporates the Dr. Ciaglia method between the thyroid and cricoid cartilages with insertion of a relatively small (5.5 mm inner diameter) air passage catheter (which does not have an inflatable sealing cuff) into the patient.

Another type of tracheostomy device and procedure is disclosed in Jacob's U.S. Pat. No. 3,682,166 and U.S. Pat. No. 3,788,326. A small, flexible, curved catheter described therein is placed over a 14 or 16 gauge needle and is percutaneously inserted through the cricothyroid membrane at about a 45°-60° angle The needle is withdrawn and the catheter is secured for transtracheal ventilation. The device and procedure are described in more detail in the publication by Dr. Jacobs et al entitled, "Transtracheal Catheter Ventilation: Clinical Experience in 36 Patients" and published in Chest, Volume 65, No. 1, January 1974, pp. 36-40.

Another somewhat related device is disclosed in U.S. Pat. No. 3,538,918 by Engelsher et al, in which a tracheo-bronchostomy tube assembly includes an outer tube and an inner tube, in which the outer tube is percutaneously inserted. The outer tube is described and illustrated as having a distal end with a bevel toward the rear of the tube. The longer inner tube is telescopically inserted into the outer tube to facilitate the removal of secretions from the broncheal passages.

A recurring problem with all of the known tracheostomy tubes of the prior art is the tendency of the distal end of the cannulae to interfere or catch on the tracheal cartilage as the tube is pushed into the trachea. Typical commercially available tubes have a distal tip which is either blunted, straight with a small annular taper or radius, beveled to the rear of the patient, or beveled to the front of the patient. For percutaneous insertion, none of these configurations are consistently free from interference with either the upper cartilage or the lower cartilage or both as the distal end of the tracheostomy tube is forced between the adjacent cartilages.

SUMMARY OF THE INVENTION

It is an object of the present invention to provide a percutaneous tracheostomy tube which can be rapidly and smoothly inserted into the trachea of a patient.

It is another object of the present invention to provide a percutaneous tracheostomy tube which is durable and dependable and insertable within a minimum sized stoma with minimum trauma to the stoma and tracheal wall so that the percutaneous insertion will not result in cosmetic deformity or infectious complications.

The present invention solves the problems of the prior art and meets the objectives by providing a tracheostomy tube which is specifically and uniquely designed for percutaneous insertion into a patient's trachea through a stoma in the neck between adjacent cartilages. The tracheostomy tube of the present invention is inserted with an inner obturator as an assembly in conjunction with the Seldinger technique utilizing a guide wire, a guiding catheter, and dilators. The tracheostomy tube includes a tubular cannula which has a central longitudinal axis, a distal portion for insertion within the trachea, and a proximal end remaining outside the trachea. The cannula is formed of relatively soft, flexible plastic material and is curved downwardly so as to position the distal portion within the trachea. The assembly includes a removable semi-rigid, substantially straight, tubular obturator which has an inner diameter adapted to fit closely over the guiding catheter and which has an outer diameter adapted to closely fit within the cannula, and has a tapered distal end which extends beyond the distal end of the cannula so that the obturator is readily inserted over the guiding catheter and between the adjacent cartilages. The distal end of the cannula is gradually tapered to form a smooth transition between the cannula and the obturator. The distal portion of the cannula has the end thereof beveled precisely to one side so that the most distal tip of the cannula is narrow, angled and tapered and is introduced by the obturator generally midway between the adjacent cartilages. Once the narrow tip of the cannula is clearly inserted between the adjacent cartilages, the remaining angled and tapered distal end of the cannula is readily eased between the cartilages free of interference to facilitate insertion of the assembly. The outer cannula preferably includes an inflatable cuff on the distal portion thereof for forming a seal between the cannula and the tracheal wall. The inflatable cuff is most preferably of the low profile configuration having the most distal attachment of the cuff everted upon the cannula to present a smooth transition between the cuff and the cannula to facilitate insertion into the trachea of the patient. The percutaneous tracheostomy tube and preparation and insertion devices are provided in a convenient kit.

BRIEF DESCRIPTION OF THE DRAWINGS

While the novel features of the invention are set forth with particularity in the appended claims, the invention will be better understood along with other features thereof from the following detailed description taken in conjunction with the drawings, in which:

DETAILED DESCRIPTION OF THE INVENTION

Figure 1:
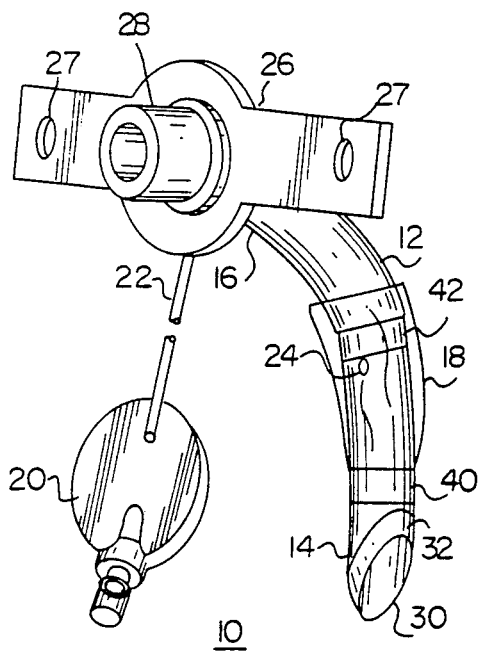
FIG. 1 is a bottom front perspective view of the percutaneous tracheostomy tube of the present invention.

Referring initially to FIG. 1, there is shown a tracheostomy tube 10 which has been specifically designed for percutaneous insertion between adjacent cartilages into the trachea of a patient. The percutaneous tracheostomy tube includes a tubular cannula 12 having a distal portion 14 for insertion into the trachea of the patient through a stoma created in the neck and a proximal end 16 remaining outside the trachea. Typical standard tracheostomy tubes are manufactured from semi-rigid polyvinyl chloride (PVC) plastic and are formed into an arc. The cannula of the present invention is manufactured from a relatively soft, flexible PVC having a hardness ranging from about 75-100 Shore A and is preferably around 80 Shore A hardness. The cannula is memorably formed into an arc in a vertical plane and has a central longitudinal axis. The relative softness and elastic flexibility permit the cannula to readily conform to the shape of an obturator and to also be adaptable in shape upon insertion through the stoma and upon any contact with the internal walls of the trachea during installation, without significant trauma to any of the contacted tissue. Once the obturator is removed, the cannula returns to its original arced configuration. The percutaneous trach tube is available in a variety of sizes (namely 6, 7, 8, and 9) corresponding to the range of average patients. Size 8, for example, has a 8.0 mm inner diameter and a 10.9 mm outer diameter, and a length of about 10 cm.

Shown attached to the distal portion 14 of the tracheostomy tube is an inflatable cuff 18 (shown deflated), which, when inflated, provides an air-tight seal between the tracheostomy tube and the inner wall of the trachea. Such sealing cuffs are described in more detail in U.S. Pat. No. 3,659,612 and U.S. Pat. No. 3,693,624, assigned to Shiley Inc. The cuff 18 is inflated by means of an air syringe (not shown) and a pressurization valve 20 extending from the proximal end 16 and which is interconnected by an inflation tube 22 and an inner lumen 24 extending from the inflation tube to a location at the distal portion 14 within the cuff. The proximal end 16 further includes an integrally molded flexible neck flange 26 which is used in conjunction with apertures 27 and a suitable strap (not shown) to secure the tracheostomy tube 10 through the neck of the patient. The proximal end 16 further includes a 15 mm standard coupler 28 adapted to readily interconnect the tracheostomy tube to a respirator system.

Figure 2:
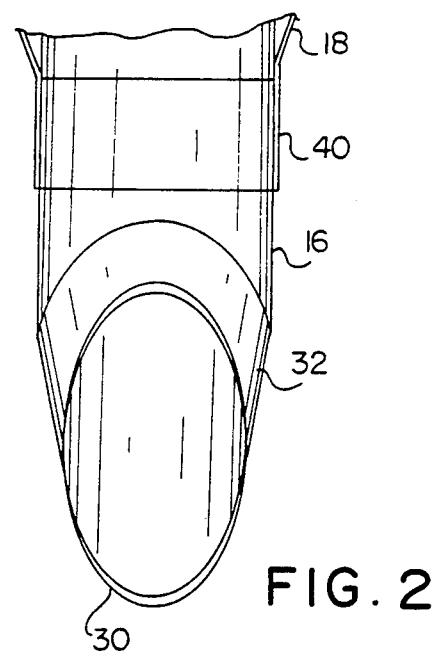
FIG. 2 is an enlarged partial right side elevational view of the distal end of the tracheostomy tube of FIG. 1.
Figure 3:
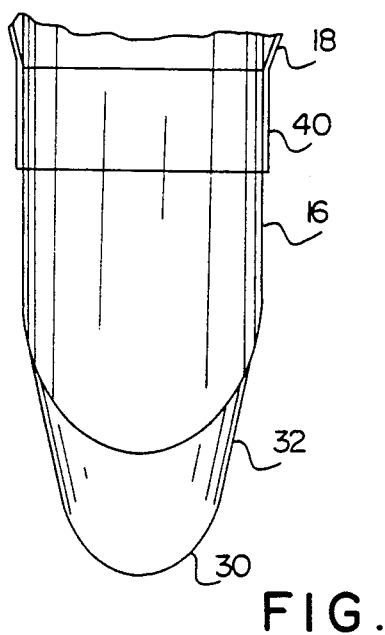
FIG. 3 is an enlarged partial left side elevational view of the distal end of the tracheostomy tube of FIG. 1.

Referring now to FIGS. 2 and 3, the distal portion 14 of the tracheostomy tube 10 is described in more detail. The distal portion 14 is considered to be a significant feature of the present invention and includes a distal end 30 which is beveled to one side (as opposed to the front or the rear) relative to the longitudinal axis. The bevel is at an angle ranging from about 15°-60° and is preferably about 45°. The bevel can be to either the left or right side of the patient, at least for the structural advantage that it provides for percutaneous insertion of the tube. In subsequent actual respiratory use of the tracheostomy tube, it may be more desirable to have the bevel to the left (as shown in FIG. 1), to facilitate directing air toward the left bronchial passage. The beveled end 30 includes a gradually tapered portion 32 which smoothly interconnects the inner diameter and the outer diameter of cannula 12 over about a 1 cm distance (approximately at a 5° angle).

Figure 4:
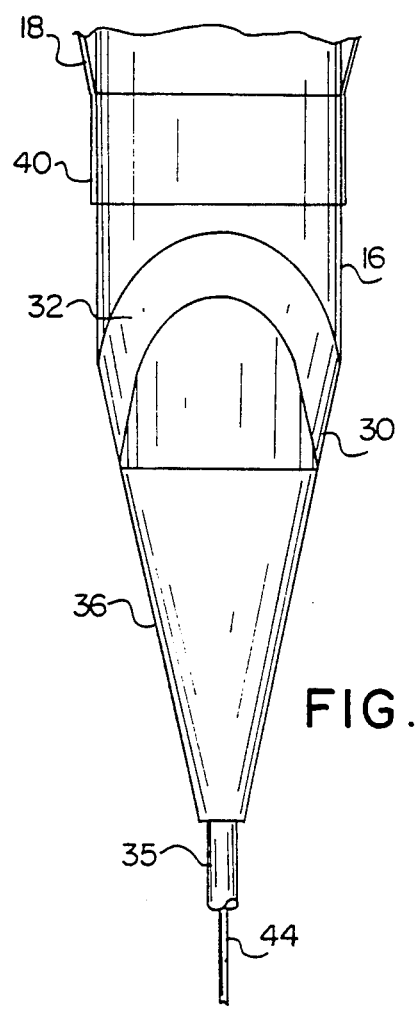
FIG. 4 is an enlarged partial right side elevational view of the distal end of the tracheostomy tube having an obturator inserted therein.
Figure 5:
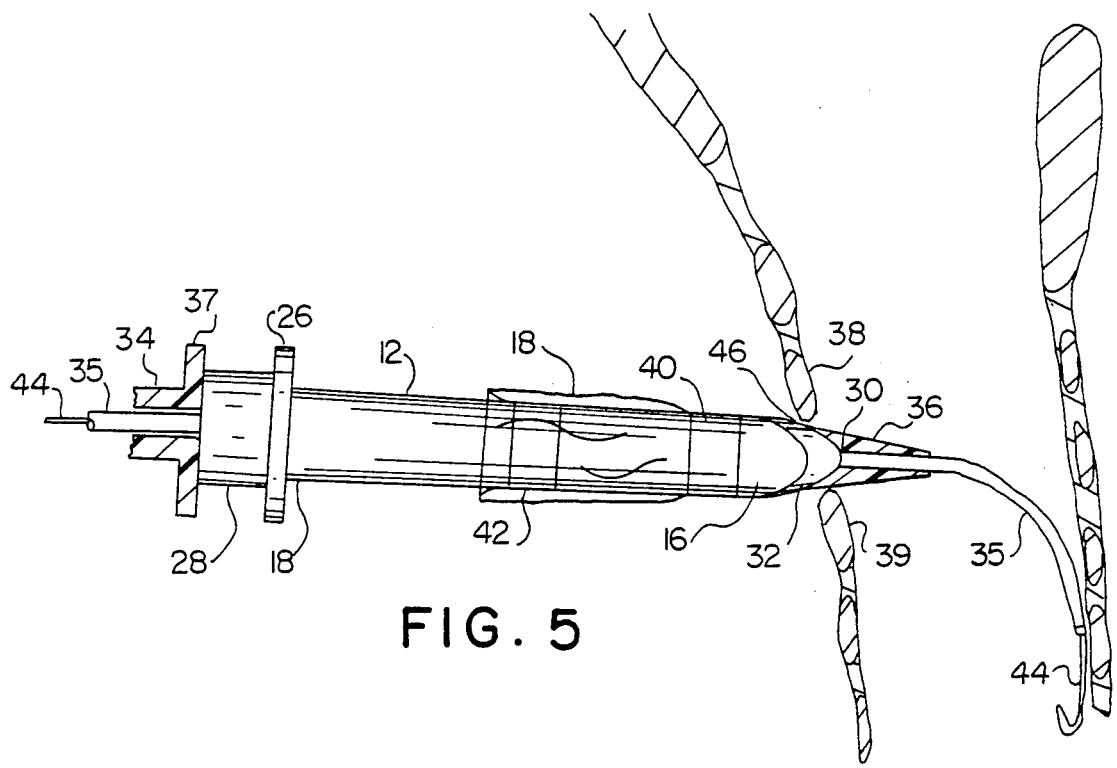
FIG. 5 is a side elevational view including a sectional view of the tracheal cartilages illustrating the initial insertion of the distal end of the percutaneous tracheostomy tube of the present invention between adjacent cartilages into the trachea of a patient (with the obturator shown in partial section)

Referring also to FIGS. 4 and 5, there is further illustrated a tubular obturator 34. The obturator 34 is formed of a semi-rigid plastic material having a hardness of about 60 Shore D and has an inner diameter about 8 French (Fr.) adapted to slide over a guiding catheter 35 (or otherwise over a first dilator) and has an outer diameter adapted to closely (but removably) fit within the inner diameter of cannula 12. The obturator is about 20 cm in length and has a distal portion 36 which is sharply tapered from its inner diameter to its outer diameter over about a 2 cm portion to form a smooth transition between the obturator and the guiding catheter 35. The outer diameter of the obturator 34 fits closely within the distal end 30 of the outer cannula 12 and the tapered portion 32 provides a smooth transition between the obturator 34 and the outer cannula 12 to facilitate insertion of the tracheostomy tube between two adjacent cartilages, such as, 38 and 39. A preferable feature of the obturator is a unique outwardly extended annular flange 37 on the proximal portion. The flange 37 (shown annular, but could be of any suitable step or cross-sectional shape) is adapted to engage the proximal end (coupler 28) of the tracheostomy tube to limit the length that the obturator can be inserted into the cannula 12. This is particularly important to insure a desired longitudinal alignment of the extended tapered distal end of the obturator 36 with the distal end 30 of the cannula to facilitate insertion of the tube. More importantly, the flange 37 prevents the sharply tapered and relatively rigid obturator from being overly inserted too far beyond the end of the cannula to possibly injure the rear tracheal wall of the patient. The obturator is initially provided substantially straight, but can be bent into a desired curved configuration as preferred or required to facilitate insertion into the trachea.

Figure 6:
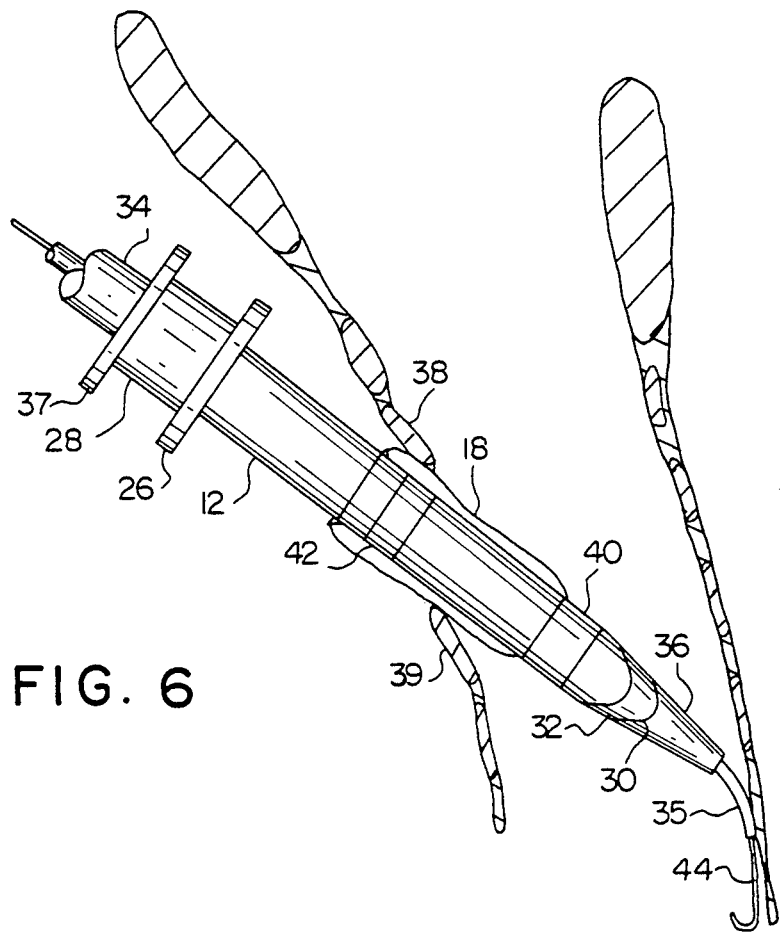
FIG. 6 is a side elevational view, similar to FIG. 5, with the tube further inserted and with the distal end rotated downwardly.

Referring particularly to FIGS. 1, 5 and 6, there is illustrated another feature of the invention which was previously briefly discussed as the inflatable cuff 18. The inflatable cuff is generally described as a cylindrical elastic membrane material which is attached to the distal portion of the outer cannula at a most distal annular attachment 40 and at a less distal annular attachment 42. In many tracheostomy tubes, the attachments 40 and 42 are made with the ends of the tubular material inverted within the cuff for various manufacturing, functional and appearance purposes. In the present invention, the distal annular attachment 40 is specifically secured in an everted manner to present only a single material thickness and thereby form the low profile cuff having a more smooth transition between the outer cannula 12 and the inflatable cuff 18 to facilitate insertion of the tube into the trachea. The attachment at 42 is preferably inverted to reduce the longitudinal space required by the cuff, but this attachment is considered optional.

Referring now particularly to FIGS. 4, 5, and 6, the operation and procedure for installation of the percutaneous tracheostomy tube of the present invention will be described. The procedure is described in detail in a publication by the inventor entitled, "Bedside Percutaneous Tracheostomy: Experience with 55 Elective Procedures" by Dr. Patrick B. Hazard et al, and is published in the *Ann. Thorac. Surg.*, Vol. 45, May, 1988 (an advance copy of which is provided herewith). A brief summary of the procedure is described as follows. Initially, the head of the patient's bed is raised to about 30° and the patient's head is positioned with the neck hyperextended. The anterior neck is draped in the usual manner. The cricothyroid subcricoid, and intertracheal ring spaces are identified. The site 46 of the tracheostomy is selected based upon ease of identification and access, although the space below the second tracheal cartilage is generally preferred. The overlying skin is anesthetized with a suitable 1-2 ml of 2% lidocaine solution. The cricoid cartilage is stabilized between the thumb and forefinger of the surgeon's left hand, and a 14 gauge needle (not shown) is introduced through a mid-line puncture site at 46 into the tracheal lumen. Air is immediately aspirated into the syringe and 3-4 ml of lidocaine solution is flushed into the trachea. The syringe is then disconnected from the needle and a suitable guidewire 44, such as a 0.13 cm diameter J-tipped guide wire, is introduced through the needle into the tracheal lumen. The needle is then withdrawn leaving the wire in place. A 1 cm mid-line vertical incision is made at the entrance site 46 of the guide wire by a number 11 scalpel. The guiding catheter 35 which is suitably an 8 Fr. tapered teflon dilator is then passed over guide wire 44 into the trachea. A sharply tapered dilator (about 20 Fr.) such as obturator 34 is inserted over the guiding catheter into the trachea further dilating the stoma. This is replaced by a larger dilator (about 30 Fr.), which corresponds at least to the outer cannula diameter of the tracheostomy tube 10. The obturator 34 is then inserted through the tracheostomy tube 10 with the distal end portion 36 extended a predetermined distance beyond the distal end 30 of the cannula. Once a suitable stoma has been created, the larger dilator is removed and the percutaneous tracheostomy tube 10 and obturator 34 assembly is then advanced over the guiding catheter 35 into the trachea. As shown particularly in FIG. 5, the sharply tapered distal portion 36 of the obturator is readily inserted between two adjacent tracheal cartilages 38 and 39; however, as the obturator assembly is advanced, the diameter increases to become essentially a wedge fit as the distal end 30 of the tracheostomy tube enters between the cartilages. It is apparent from FIG. 5 that an abrupt transition between the obturator and the tracheostomy tube would surely interfere with the cartilages 38 or 39, which was the early experience utilizing standard tracheostomy tubes. Blunt, rounded and annularly tapered tubes had difficulty passing between the cartilages; also, tubes having a bevel toward the rear tended to interfere with the lower cartilage while tubes having a bevel to the front tended to interfere with the upper cartilage to resist insertion of the tube into the trachea. As shown, the beveled distal end 30 of the present invention is oriented so that the distal-most tip is essentially at one side and is narrow, angled and tapered and is introduced by the obturator approximately midway between the adjacent cartilages 38 and 39 so that the distal end 30 is initially positioned between the cartilages without interference. Once the distal end 30 is clearly between the cartilages, the tapered and angled remainder of the distal end is readily eased between the cartilages and into the trachea. Further insertion is facilitated by rotating the distal end 36 of the obturator 34 downwardly. FIG. 6 further illustrates that it may be preferable to have a downward curvature to the obturator. Similarly, as shown in FIG. 6, the smooth transition between the low profile cuff attachment 40 provides a smooth transition which is readily eased between the adjacent cartilages. Once the distal end of the inflatable cuff is between the cartilages, the cartilages are further expanded by the remainder of the cuff as it is inserted, and since the cartilages were not severed, there are no rough cartilage edges on which to rupture the cuff. The obturator 34, guiding catheter 35 and guide wire 44 are then withdrawn from the tracheostomy tube 10 and the tracheostomy tube is fully inserted within the trachea and secured by a strap through the neck flange 26 to the neck of the patient. The arcuate curvature of the cannula 12 (see FIG. 1) then elastically returns to the tracheostomy tube and the tube is then properly positioned within the trachea. The cuff can then be inflated and the tube can be attached to a respirator system.

Figure 7:
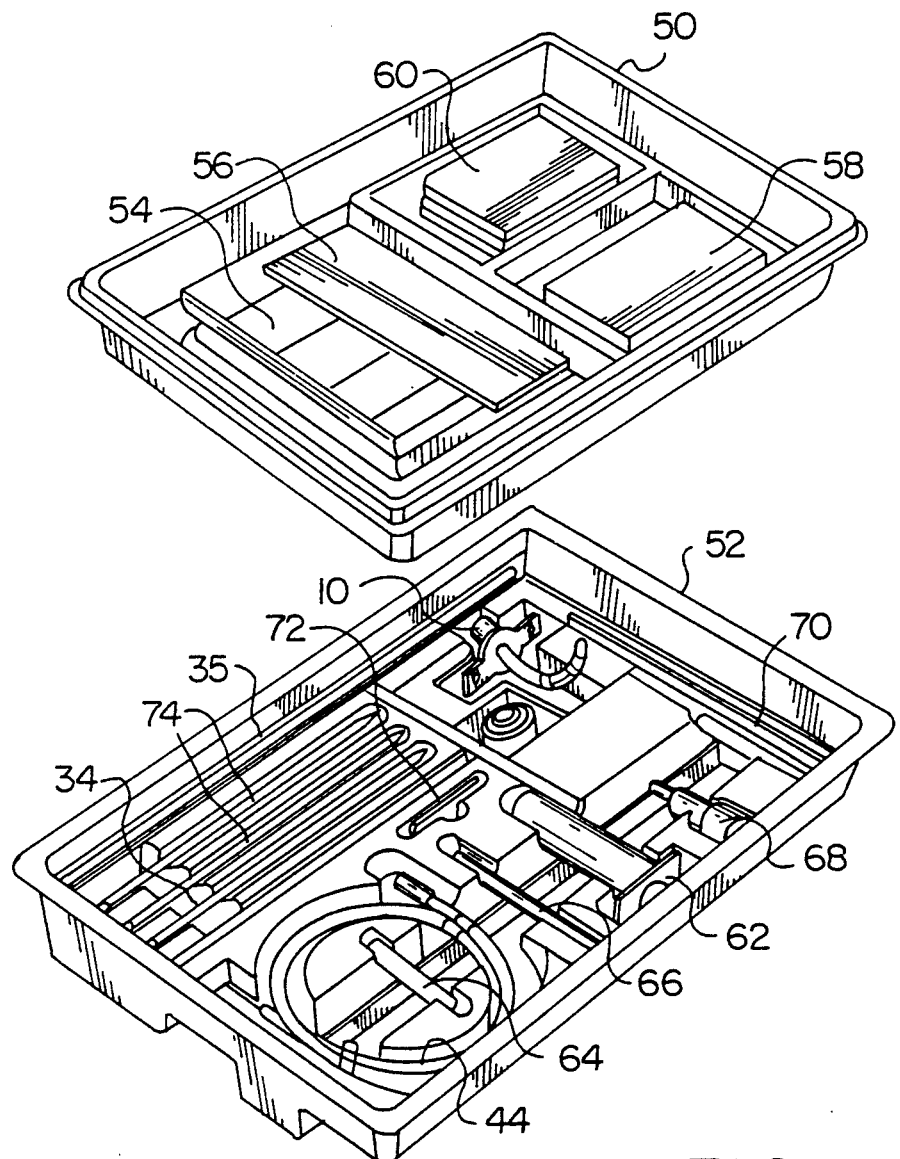
FIG. 7 is an upper front perspective view of a percutaneous tube kit illustrating an insertable upper tray exploded from a lower tray.

The percutaneous tracheostomy tube of the present invention is available by Shiley Incorporated, Irvine, Calif. and is conveniently packaged as a percutaneous tracheostomy kit as shown in FIG. 7. The kit includes an upper tray 50 containing the patient preparation components, which is enclosed within the upper portion of a lower tray 52 containing the tracheostomy procedure components. The trays are nested together and are sealed within a suitable peel-away Tyvek lidding stock material (not shown). Upon peeling back the lid, the upper tray 50 is exposed which has vacuum formed compartments for segregating and retaining the preparator components, to include: suitable drapes 54 i.e., a U-shaped neck drape 30"×30", and a face drape 30"×12"; a pair of gloves 56, i.e. size 8 latex; a pack of saturated antiseptic swabsticks 58; and appropriate gauze sponges 60 (about five 4"×4"). After the patient is prepared, the upper tray is removed exposing the lower tray 52. The lower tray includes vacuum formed compartments therein for segregating and retaining the procedure components. The components include: an injection syringe 62, at least one is required and can be used with anesthetic needles 64 and with insertion needle 66, or two syringes can preferably be provided for each specific injection task; one or two viles of anesthetic 68, i.e. 10 cc of 2% lidocaine solution; a scalpel 70, i.e. a number 11 blade in a plastic handle; the guide wire 44, shown coiled; a first short tubular dilator 72, about 10 Fr.; the guiding catheter 35; a pair of tubular, sharply tapered dilators 74, about 20 cm in length and ranging in diameter in correlation with the size of the tracheostomy tube (i.e., no. 7 tube utilizes a 25 Fr. and a 30 Fr. dilator in addition to the 10 Fr. first dilator 72, and 17 Fr. guiding catheter 35 common to all sized tracheostomy kits); and the kit finally includes the tracheostomy tube 10 with neck strap and the obturator 34 (in which the obturator 34 can also be used as an intermediate dilator, if necessary).

The unique configuration of the tracheostomy tube 10 of the present invention along with the obturator 34, permit this entire procedure to be technically simple and generally requires only a few minutes to perform. The unique packaging of the components into a nested two-tray disposable kit further contributes to the speed and cleanliness of the preparation and procedure to further reduce the probability of complications. The virtual absence of infectious complications is especially advantageous. In addition, the procedure can be performed at the bedside and does not require exposure of the patient to the risks of transportation outside the intensive care unit. Finally, the cosmetic deformity after decannulation is trivial. It is further considered that the lack of tracheal destruction and infections associated with the percutaneous techniques likely diminish the subsequent risk of stenosis.

While specific embodiments of the present invention have been illustrated and described herein, it is realized that modifications and changes will occur to those skilled in the art. It is therefore to be understood that the appended claims are intended to cover all such modifications and changes as fall within the true spirit and scope of the invention.

I claim:

1. A tracheostomy tube for use with an obturator for percutaneous insertion into a patient's trachea through a stoma in the neck between adjacent cartilages to assist breathing comprising:

a tubular cannula having a central longitudinal axis, a distal portion for percutaneous insertion within the trachea, and a proximal end remaining outside the trachea;

said cannula formed of relatively soft flexible plastic material and curved downwardly so as to position said distal portion within the trachea;

said distal portion having an end which is gradually tapered for forming a smooth transition with the obturator and which is beveled to one side relative to the longitudinal axis so that the most distal tip of said beveled end is narrow, angled and tapered and is introduced generally midway between the adjacent cartilages and the remaining angled and tapered distal end is readily eased between the cartilages free of interference to facilitate insertion of said tube.

2. The tracheostomy tube as in claim 1 further comprising a ventilation coupling on said proximal end and an inflatable cuff on said distal portion for forming a seal with the tracheal wall.

3. The tracheostomy tube as in claim 2 wherein said cannula is formed of a radiopaque material.

4. The tracheostomy tube as in claim 2 wherein said cannula is formed of flexible polyvinyl chloride having about 75-100 Shore A hardness.

5. The tracheostomy tube as in claim 2 wherein said end is beveled for directing air to the left side of the trachea of the patient.

6. The tracheostomy tube as in claim 2 wherein said end is beveled for directing air to the right side of the trachea of the patient.

7. The tracheostomy tube as in claim 2 wherein said cuff is a low-profile configuration.

8. A tracheostomy tube and obturator assembly for use with a guide wire for percutaneous insertion into a patient's trachea through a stoma in the neck between adjacent cartilages to assist breathing, comprising:

a soft, flexible, curved, tubular cannula having a distal portion for percutaneous insertion within the trachea, and a proximal end for remaining outside the trachea;

a removable tubular obturator having a distal portion for insertion into said cannula and a proximal portion remaining outside said cannula and having the outer surface adopted to closely fit within said cannula, and having a generally tapered distal end extending beyond said distal end of said cannula so that said obturator is readily inserted between the adjacent cartilages;

said distal end of said cannula being gradually tapered forming a smooth transition between said cannula and said obturator; and said distal portion of said cannula having the end thereof beveled to one side so that the most distal tip of said cannula is narrow and angled and is introduced by said obturator generally midway between the adjacent cartilages and the remaining angled and tapered distal end of said cannula is readily eased between the cartilages free of interference to facilitate insertion of the assembly.

9. The tracheostomy tube and obturator assembly as in claim 8 wherein the proximal portion of said obturator further includes an outwardly extended flange adapted to engage the proximal end of said cannula to limit the length that said distal portion of said obturator is extendable beyond the distal end of said cannula.

10. The assembly as in claim 9 wherein said flange is adapted so that only said tapered distal end of said obturator is extendable beyond said distal tip of said cannula.

11. The tracheostomy tube and obturator assembly as in claim 8 further comprising a ventilation coupling on said proximal end of said cannula and an inflatable cuff on said distal portion of said cannula for forming a seal with the tracheal wall.

12. The tracheostomy tube and obturator assembly as in claim 11 wherein said cannula is formed of a radiopaque material.

13. The tracheostomy tube and obturator assembly as in claim 11 wherein said cannula is formed of flexible polyvinyl chloride ranging from about 75-100 Shore A hardness.

14. The tracheostomy tube and obturator assembly as in claim 11 wherein said end is beveled for directing air to the left side of the trachea of the patient.

15. The tracheostomy tube and obturator assembly as in claim 11 wherein said end is beveled for directing air to the right side of the trachea of the patient.

16. The tracheostomy tube and obturator assembly as in claim 11 wherein said cuff is a low profile configuration having the most distal attachment of said cuff everted upon the cannula to present a smooth transition between said cuff and said cannula to facilitate insertion.

17. The tracheostomy tube and obturator assembly of claim 11 wherein said obturator is substantially straight and is formed of a semi-rigid plastic material.

18. The tracheostomy tube and obturator assembly as in claim 11 packaged as a kit further including an upper tray enclosing patient preparation components,
said upper tray nested in the upper portion of a lower tray further including percutaneous tracheostomy procedure components, and
said upper and lower trays enclosed within a removable cover.

19. The kit as in claim 18 consisting essentially only of:
said upper tray further including,
drape means,
surgical gloves,
antiseptic means,
gauze sponge means,
and said lower tray further including,
said tracheostomy tube,
said obturator,
scalpel means,
syringe means,
injector needle means,
insertion needle means,
anesthetic solution means,
guide wire means, and
dilator means.

20. The kit as in claim 19 wherein said dilator means includes said obturator utilized initially as a dilator, and a final dilator at least as large in diameter as said cannula.

21. The kit as in claim 19 wherein said dilator means further comprises guiding catheter means.

22. The kit as in claim 21 wherein said dilator means further includes an initial dilator of about 10 French or insertion prior to insertion of said guiding catheter means.

* * * * *